United States Patent
Bedard et al.

(10) Patent No.: US 9,392,933 B2
(45) Date of Patent: Jul. 19, 2016

(54) OTOSCOPE ILLUMINATION

(71) Applicants: Noah Bedard, San Francisco, CA (US); Lingfei Meng, Redwood City, CA (US)

(72) Inventors: Noah Bedard, San Francisco, CA (US); Lingfei Meng, Redwood City, CA (US)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/323,949

(22) Filed: Jul. 3, 2014

(65) Prior Publication Data

US 2015/0250381 A1  Sep. 10, 2015

Related U.S. Application Data

(60) Provisional application No. 61/949,117, filed on Mar. 6, 2014.

(51) Int. Cl.
| | | |
|---|---|---|
| A61B 1/227 | (2006.01) | |
| A61B 1/32 | (2006.01) | |
| A61B 5/00 | (2006.01) | |
| A61B 1/00 | (2006.01) | |
| A61B 1/06 | (2006.01) | |
| G02B 23/24 | (2006.01) | |

(52) U.S. Cl.
CPC ............ *A61B 1/227* (2013.01); *A61B 1/00096* (2013.01); *A61B 1/00186* (2013.01); *A61B 1/0607* (2013.01); *A61B 1/0676* (2013.01); *A61B 1/0684* (2013.01); *A61B 5/6817* (2013.01); *G02B 23/2461* (2013.01); *G02B 23/2469* (2013.01)

(58) Field of Classification Search
CPC ........ A61B 1/227; A61B 1/32; A61B 5/6817; A61B 5/0075; A61B 5/0062; A61B 5/0082
USPC .................. 600/101–183, 476–480
See application file for complete search history.

(56) References Cited

U.S. PATENT DOCUMENTS

| | | | |
|---|---|---|---|
| 3,874,371 A | 4/1975 | Stader et al. | |
| 3,934,578 A | 1/1976 | Heine | |
| 3,978,850 A | 9/1976 | Moore et al. | |
| 4,006,738 A | 2/1977 | Moore et al. | |
| 4,567,881 A | 2/1986 | Heller | |
| 4,914,556 A * | 4/1990 | Richardson | F21V 9/10 359/888 |
| 5,658,235 A | 8/1997 | Priest et al. | |
| 5,919,130 A | 7/1999 | Monroe et al. | |
| 6,110,106 A * | 8/2000 | MacKinnon | A61B 5/0071 600/160 |
| 6,475,138 B1 | 11/2002 | Schechter et al. | |
| 7,986,342 B2 | 7/2011 | Yogesan et al. | |
| 8,469,882 B2 | 6/2013 | Andreassen et al. | |
| 8,949,078 B2 | 2/2015 | Berkner et al. | |
| 2003/0187331 A1 * | 10/2003 | Faludi | A61B 1/0607 600/200 |
| 2009/0292168 A1 * | 11/2009 | Farr | A61B 1/0607 600/109 |
| 2013/0123641 A1 * | 5/2013 | Goldfain | A61B 5/0066 600/476 |
| 2013/0128223 A1 * | 5/2013 | Wood | A61B 1/227 351/206 |
| 2013/0296652 A1 | 11/2013 | Farr | |
| 2014/0206979 A1 | 7/2014 | Berkner et al. | |
| 2014/0316238 A1 | 10/2014 | Berkner et al. | |

OTHER PUBLICATIONS

Ng et al. "Light Field Photography with a Hand-held Plenoptic Camera" Standford tech Report, (2005), pp. 1-11.*
U.S. Appl. No. 61/754,327, filed Jan. 18, 2013.

* cited by examiner

*Primary Examiner* — Pedro Philogene
(74) *Attorney, Agent, or Firm* — Fenwick & West LLP (57) ABSTRACT

Various types of illuminators for plenoptic otoscopes. The illuminators provide illuminating light to image the inside of the ear.

16 Claims, 9 Drawing Sheets

OTOSCOPE ILLUMINATION

CROSS-REFERENCE TO RELATED APPLICATION(S)

This application claims priority under 35 U.S.C. §119(e) to U.S. Provisional Patent Application Ser. No. 61/949,117, "Otoscope illumination," filed Mar 6, 2014. The subject matter of the foregoing is incorporated herein by reference in its entirety.

BACKGROUND OF THE INVENTION

1. Field of the Invention

This invention relates generally to otoscopes for imaging the inside of human or animal ears.

2. Description of the Related Art

Otoscopes are a common imaging device that clinicians use to diagnose diseases of the middle ear. While otoscopes range in complexity from simple magnifiers to high-definition digital cameras, their basic functionality has remained the same for many years. They simply deliver a magnified image of the middle ear. Recently, there has been interest in leveraging advances in plenoptic camera technology to build an otoscope that captures a three-dimensional depth profile (or lightfield) of the middle ear, possibly with additional multispectral information. However, capturing lightfield data places additional requirements on the illumination compared to traditional otoscopes.

Thus, there is a need for better illumination sources for otoscopes, particularly for plenoptic otoscopes.

SUMMARY

One aspect includes a plenoptic otoscope with an illuminator located at a base of the speculum. The illuminator includes light sources arranged around a periphery of the base of the speculum. The light sources illuminate the inside of the ear.

Another aspect includes a plenoptic otoscope with an illuminator positioned to produce illuminating light that propagates along the optical train of the plenoptic otoscope. The plenoptic otoscope further includes a filter module that includes a central clear area and a plurality of spectral filters arranged around the central clear area. The illuminator produces white light that propagates through the central clear area of the filter module to the inside of the ear. In another arrangement, the white light propagates to the inside of the ear, but without propagating through the filter module.

Other aspects include components, devices, systems, improvements, methods, processes, applications and other technologies related to the foregoing.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed. To facilitate understanding, identical reference numerals have been used where possible, to designate identical elements that are common to the figures.

A plenoptic otoscope design can overcome the poor data quality of current otoscopes for feature extraction for otitis diagnosis. For example, a plenoptic otoscope can be used to capture three-dimensional (3D) shapes, translucency, and/or detailed color information. Bright and spatially uniform illumination is important for otoscopes. A plenoptic otoscope additionally benefits if (1) the illumination source does not obstruct any portion of the imaging path, (2) the illumination is broadband and spatially/spectrally uniform to provide simultaneous acquisition of multispectral data, and (3) specular reflections are minimized to improve image analysis.

Figure 1A:
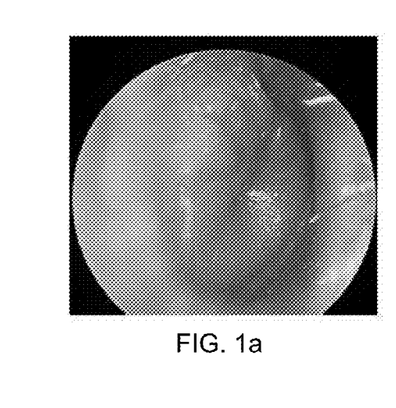
FIGS. 1a-c (prior art) are example images showing different conditions of the ear as well as features to distinguish the conditions.
Figure 1B:
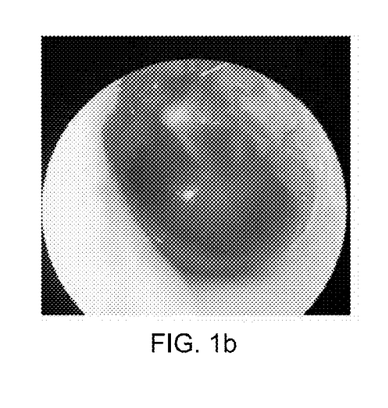
Figure 1C:
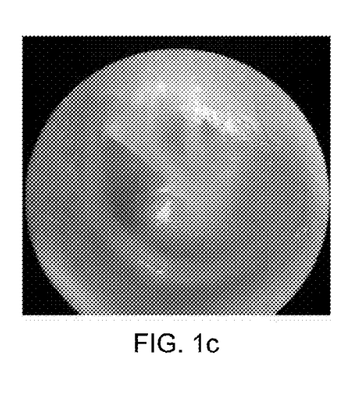

FIGS. 1a-c (prior art) are example images showing different conditions of the ear as well as features to distinguish the conditions. The three conditions shown are acute otitis media (AOM) in FIG. 1a, otitis media with effusion (OME) in FIG. 1b, and otitis media with no effusion (NOE) in FIG. 1c. Table 1 lists some features distinguishing the conditions. More specifically, Table 1 lists otoscopic findings on tympanic membrane (TM) images associated with the above three conditions.

TABLE 1

Otoscopic findings associated with clinical diagnostic categories of TM images

|  | AOM | OME | NOE |
| --- | --- | --- | --- |
| Color | White, pale yellow, markedly red | White, amber, gray, blue | Gray, pink |
| Position | Distinctly full, bulging | Neutral, retracted | Neutral, retracted |
| Translucency | Opacified | Opacified, semi-opacified | Translucent |

As can be seen from FIGS. 1a-c and Table 1, the three conditions of the ear are different and they can be distinguished from one another based on one or more of the following features: color, position (e.g., 3D shape), and translucency. In order to make correct diagnosis of the ear condition, otoscopic images capturing accurate information about color, 3D shape and translucency of an inside of an ear (e.g., a tympanic membrane in an ear canal) are desirable.

Figure 2:
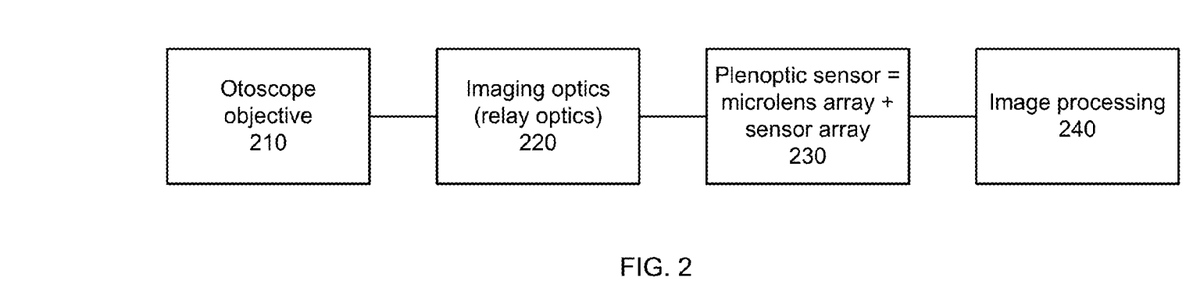
FIG. 2 is a block diagram of a plenoptic digital otoscope system.

FIG. 2 is a block diagram of a plenoptic digital otoscope system. The system includes an otoscope objective 210, imaging optics (relay optics) 220, a plenoptic sensor 230 and image processing 240. The otoscope objective 210 can be an imaging objective, as used in conventional otoscopes. The imaging optics 220 works in conjunction with the otoscope objective 210 to form a conventional image within the otoscope instrument. Rather than a conventional sensor array capturing this image, a plenoptic sensor 230 captures the image. The plenoptic sensor 230 is a sensor array with a microimaging array (e.g., a microlens array or pinhole array) mounted in front of it. In addition, a filter module (not shown in FIG. 2) can be inserted at a pupil plane of the optical train (or at one of its conjugates) to allow spectral or other filtering of the light. The digital information extracted by the plenoptic sensor 230 is sent to a computing module 240 that performs the image processing of the plenoptic data. In this way, three-dimensional and/or spectral data can be extracted.

Figure 3A:
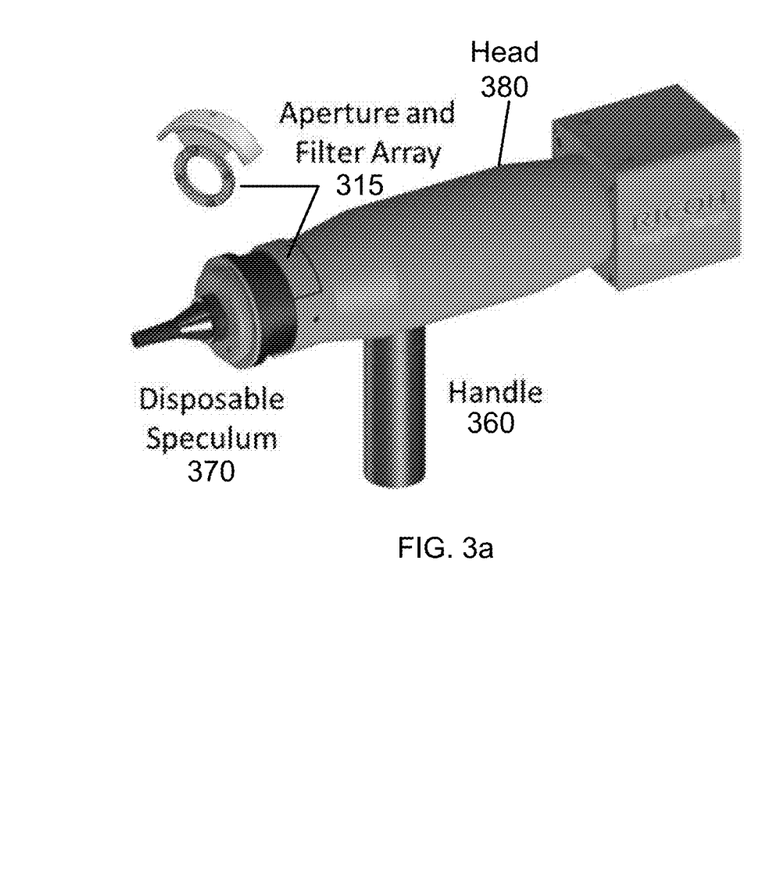
FIGS. 3a-b show a perspective view and a cut-away view of a plenoptic otoscope.
Figure 3B:
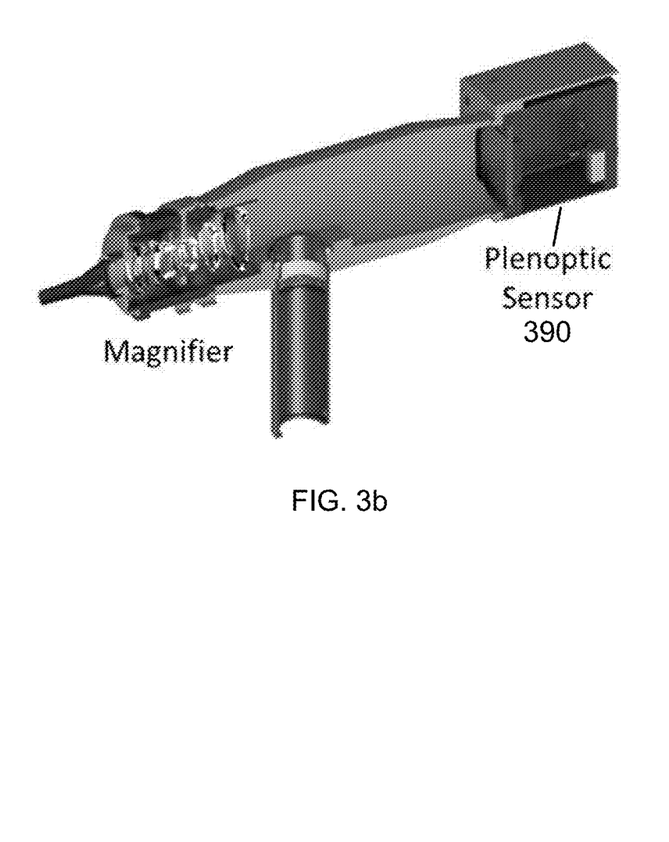

FIGS. 3a-b show a perspective view and a cut-away view of a plenoptic otoscope. In particular, note that the plenoptic otoscope includes a filter array 315 and a plenoptic sensor 390. The filter array 315 can be inserted into the optical train of the plenoptic otoscope. FIG. 3a shows the filter array 315 separately and also as inserted into the otoscope. Examples of additional plenoptic otoscope designs are described with respect to FIGS. 8-12 below.

The plenoptic otoscope head 380 can be mounted on top of a handle 360 that houses an illumination source (e.g., portable system) or can be connected to an illumination source (e.g., wall-mounted system). The otoscope illumination source may be an LED light source, a standard white illumination source, etc. The illumination source may have polarization characteristics as well. For example, it may emit unpolarized, partially polarized, or completely polarized (e.g., TE, TM) light.

Figure 4A:
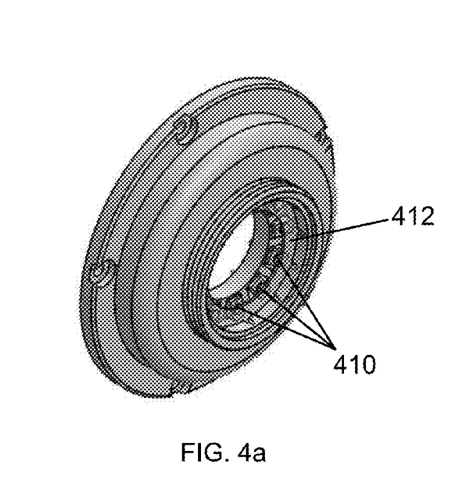
FIGS. 4a-c show an illuminator design that uses a ring of LEDs.
Figure 4B:
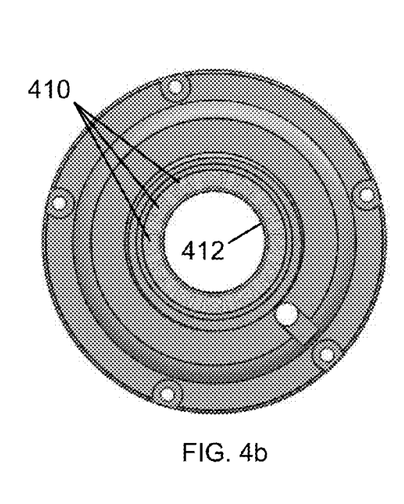
Figure 4C:
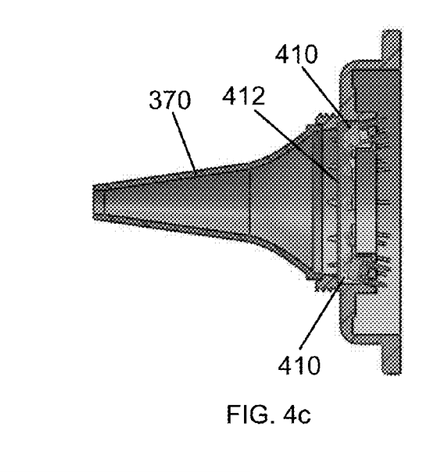

FIGS. 4a-c show an illuminator design that uses a ring of LEDs 410 mounted at the base of the speculum 370. FIG. 4a is a perspective view of the base without the speculum. FIG. 4b is a front view of the base without the speculum. FIG. 4c is a side cutaway view of the base with speculum. In this example design, there are 12 LEDs arranged in a circular pattern. This is most clearly seen in the front view of FIG. 4b. In addition, the LEDs are angled inward, toward the distal tip of the speculum, to help maximize light throughput. This can be seen in the side view of FIG. 4c. Additionally, the areas around the LEDs are coated with a reflective membrane to send light forward toward the tip. Stray light is reduced by using a matte black finish on the inner surface of the speculum. Finally, specular reflections are blocked with a ring-shaped linear polarizer 412 mounted in front of the LEDs in combination with an orthogonal linear polarizer placed at the aperture or sensor.

Figure 5:
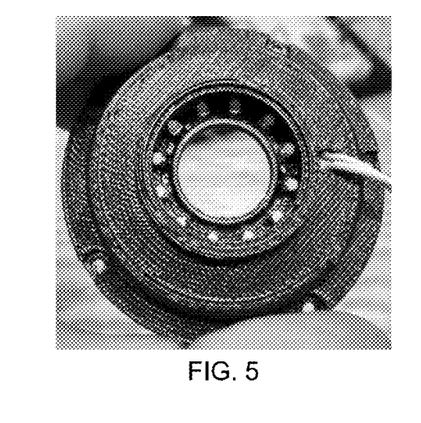
FIG. 5 is a photograph of the illuminator of FIG. 4.
Figure 6:
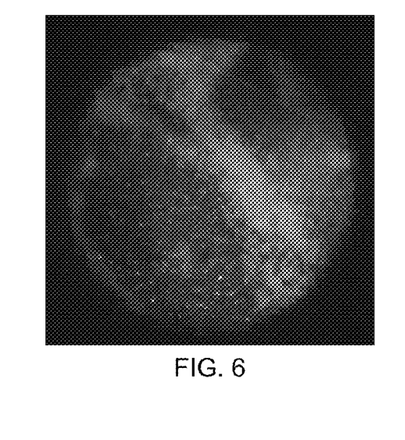
FIG. 6 is an image of an ear model as seen through the speculum.

A prototype of the ring-LED design is shown in FIG. 5. The ring mount contains 12 warm white 1.8 mm LEDs that each emit approximately 1200 mCd. The warm white 3000K color temperature was chosen because it has a relatively uniform spectral distribution throughout the visible band. The aperture is large enough to pass all lightfield rays in our system, yet small enough for LEDs to transmit light through the speculum tip. FIG. 6 shows an image of an ear model as seen through the speculum.

As a variation of this technique, the ring illumination can be implemented with optical fibers rather than LEDs. As another variation, the speculum can be fabricated out of a material that acts as a waveguide. This can help direct light from the ring illuminator to the tissue.

Figure 7A:
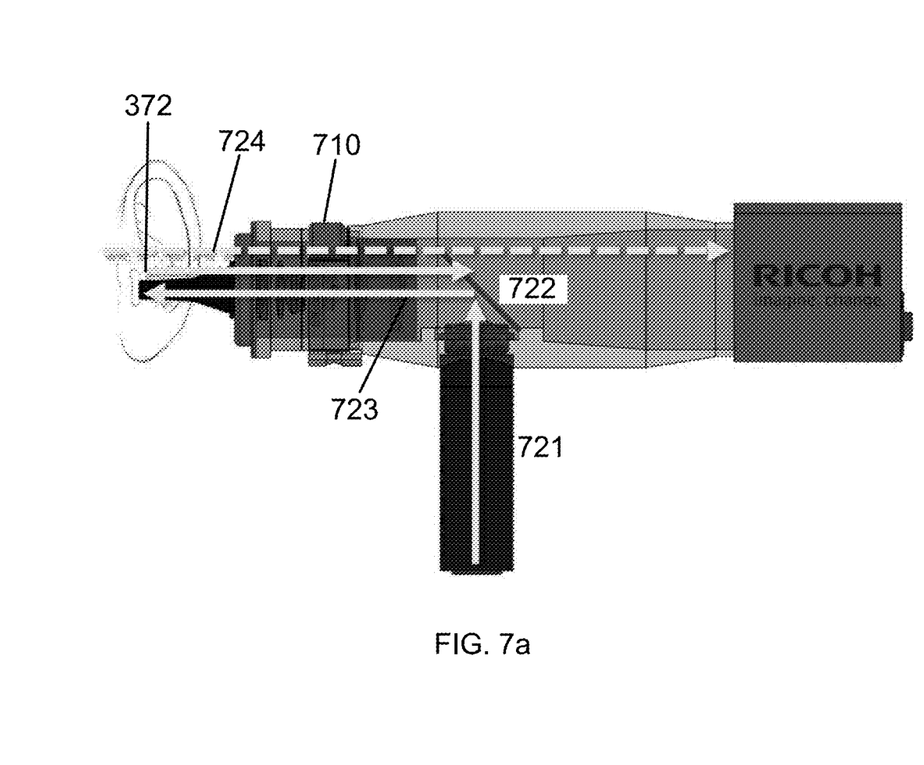
FIGS. 7a-b show an illuminator design that uses a filter array with a central aperture.
Figure 7B:
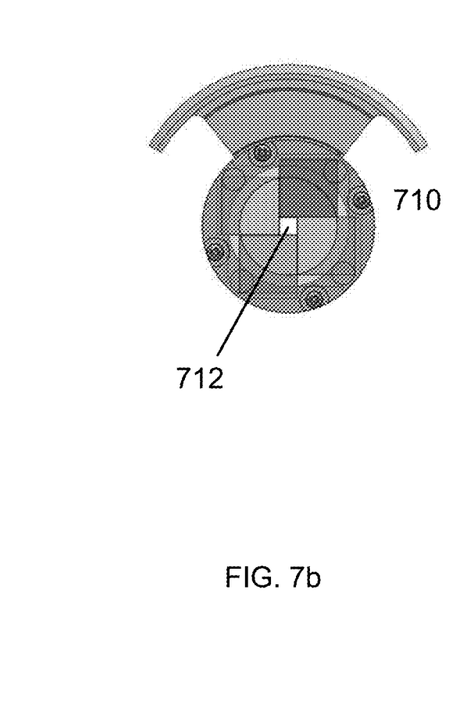

FIGS. 7a-b show an alternate design that uses a polarizing beamsplitter plate (PBSP) to direct light toward the middle ear. FIG. 7a is a cut-away side view that shows the optical path within the otoscope. FIG. 7b is a front view of the filter array 710. The filter array includes four color filters and a central clear area 712. This design allows the light source to reside away from the speculum and magnification optics. The design is adapted for use with polarization and multispectral plenoptic imaging.

A white light source placed within the otoscope handle is linearly polarized. A lens sends the light 721 toward a PBSP 722, which reflects 723 the converging polarized rays onto a small opening 712 within the filter module 710. After passing through the opening, the rays diverge and create a fairly uniform illumination spot centered on the speculum tip 372. Light scattered and reflected 724 from the middle ear return to the aperture 710, where they pass through the opening 712 as well as adjacent spectral filters. Rays are then incident on the PBSP, which only transmits rays that have changed polarization states (by scattering deep into tissue). This configuration provides both uniform illumination and reduced specular reflections.

Figure 7C:
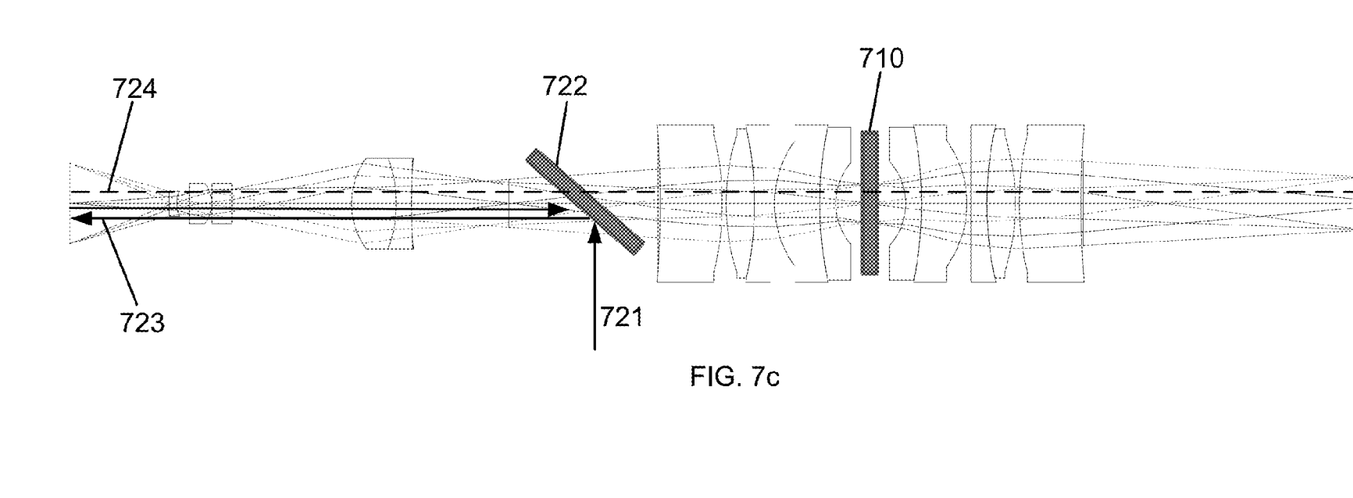
FIG. 7c shows yet another illuminator design.

FIG. 7c shows an alternate design, where the positions of the filter module 710 and beamsplitter 722 are reversed. That is, in FIG. 7a, the components are arranged in the following order from speculum tip to plenoptic sensor: otoscope objective, filter module 710 and beamsplitter 722. In FIG. 7c, the components are arranged in the following order: otoscope objective, beamsplitter 722 and filter module 710. As a result, the filter module 710 in FIG. 7c can function without a central clear area because it is not required to pass white light.

Figure 8:
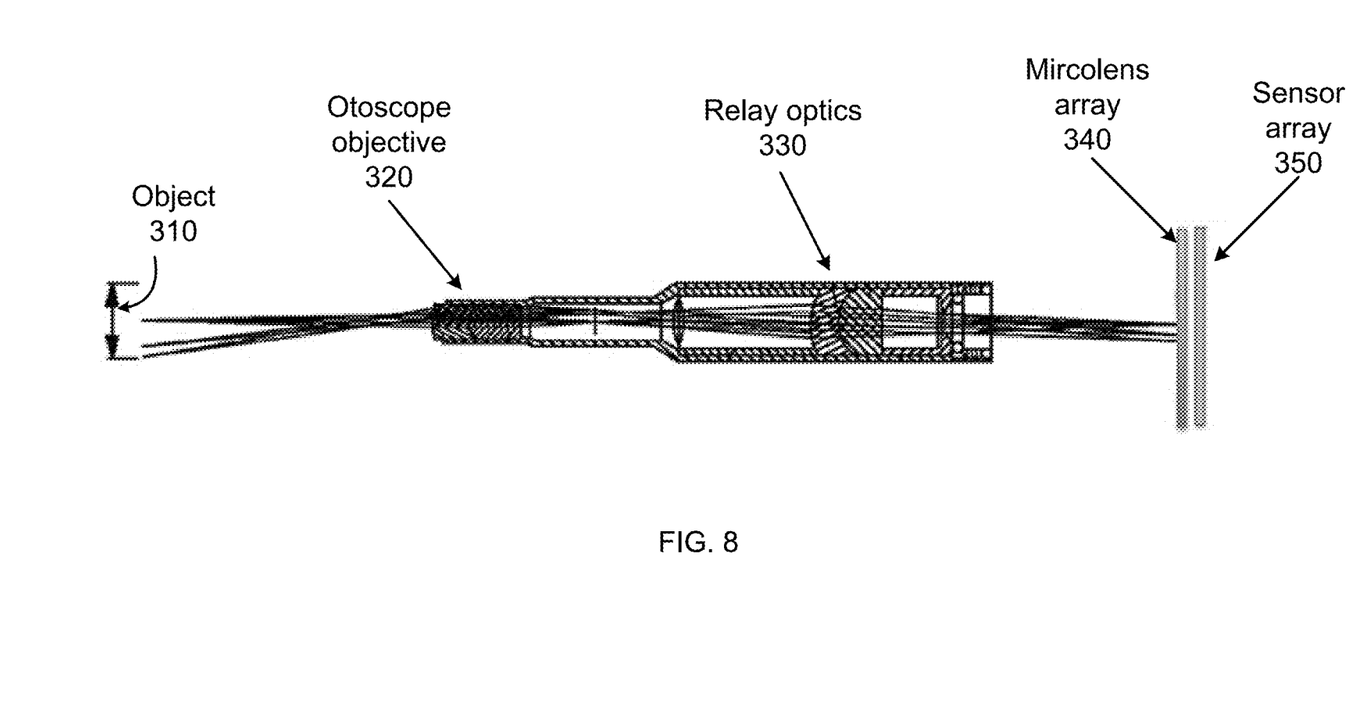
FIG. 8 shows an optical train of a plenoptic otoscope.

FIGS. 8-12 show additional designs of plenoptic otoscopes. FIG. 8 shows an optical train of a plenoptic otoscope. The plenoptic otoscope includes two parts: a primary imaging system and a plenoptics sensor. The primary imaging system includes an otoscope objective 320 and relay optics 330. They cooperate to form a conventional image of an object 310 (e.g., an inside of an ear, a tympanic membrane, etc.). A plenoptic sensor (a microlens array 340 and a sensor array 350) is positioned so that the microlens array 340 is located in the conventional image plane, which is an intermediate image plane of the primary imaging system. The sensor array 350 then captures lightfield data, which will be referred to as the plenoptic image of the object 310.

In one embodiment, the plenoptic image contains depth data. A computing module (not shown in FIG. 8) further processes the captured plenoptic image to produce three-dimensional data. This operational mode of the plenoptic otoscope may be referred to as a depth imaging mode. For example, in the depth imaging mode, the plenoptic image captured by the sensor array 350 may be processed to provide a three-dimensional depth image of an inside of an ear.

Figure 9A:
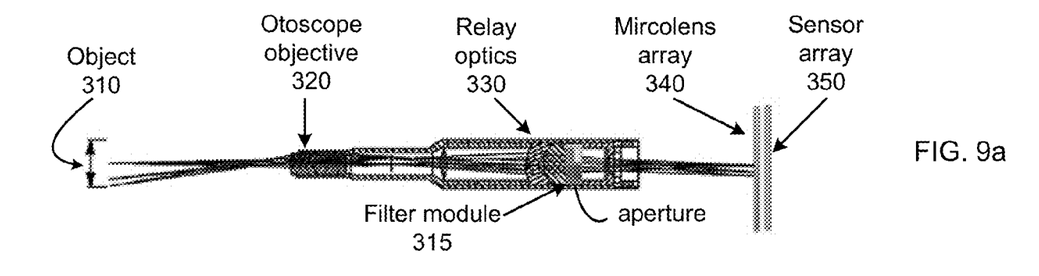
FIGS. 9a-c show optical trains of a plenoptic otoscope with filtering.
Figure 9B:
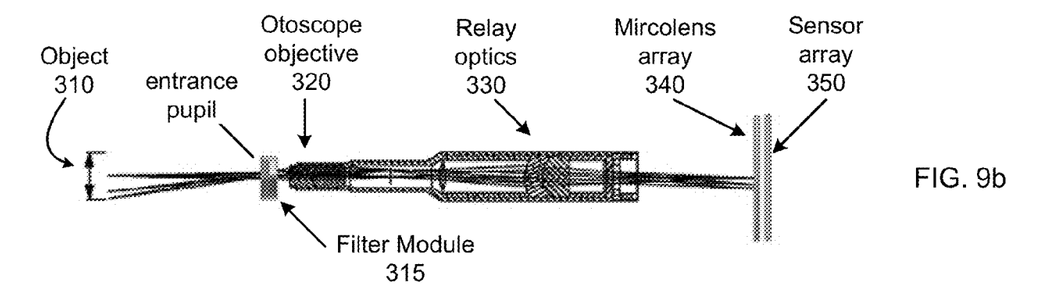
Figure 9C:
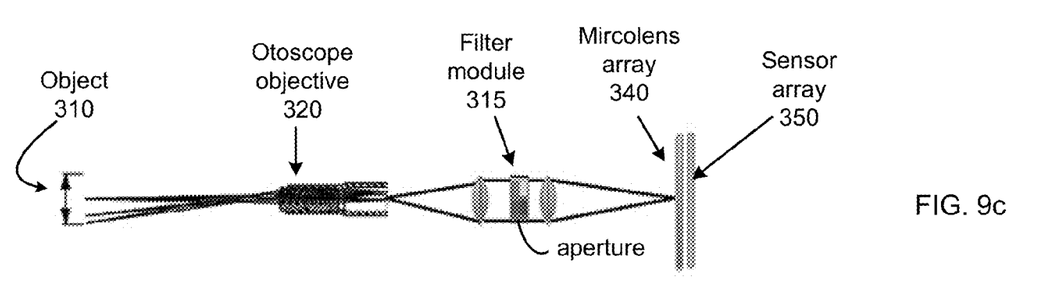

Another possible operational mode of the plenoptic otoscope is a spectral imaging mode. In the spectral imaging mode, the plenoptic image captured by the sensor array 350 contains spectral information and may be processed to provide two or more different spectral images of the object 310. In one embodiment, spectral imaging can be enabled by placing a filter module at a pupil plane conjugate of the plenoptic otoscope, as shown in FIGS. 9a-c. The term "pupil plane conjugate" is used to refer to any plane that is a pupil plane of the primary imaging system or a conjugate plane of that pupil plane. For example, the term pupil plane conjugate includes the entrance pupil plane and the exit pupil plane of the primary imaging system.

FIGS. 4a-c show different placements of the filter module. In FIG. 4a, the filter module 315 is located at an aperture between the relay optics and the plenoptic sensor. In FIG. 4b, the filter module 315 is located at the entrance pupil. In FIG. 9c, the filter module 315 is located at an aperture between a pair of relay lenses. In each of the embodiments shown in FIGS. 9a-c, the filter module 315 is positioned at a pupil plane conjugate.

In one implementation of FIG. 9b, the filter module is contained in a detachable tip (or ring), which is attached to the plenoptic otoscope. When the tip is attached, the filter module is positioned at the entrance pupil of the first lens group, as shown in FIG. 9b. As in a conventional otoscope, a speculum used to enter the ear canal may be attached to the detachable tip.

Figure 10A:
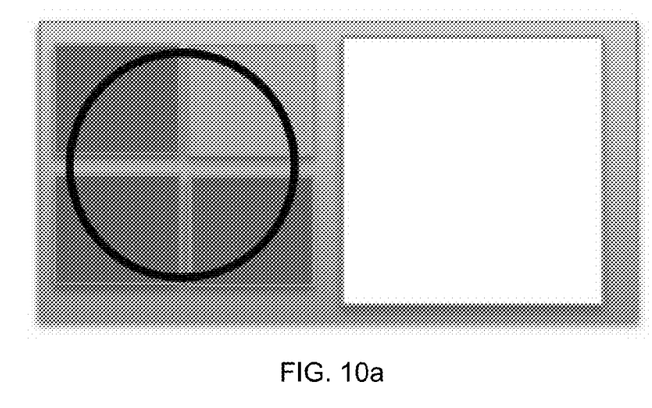
FIGS. 10a-b show use of a filter module with different spectral filters.
Figure 10B:
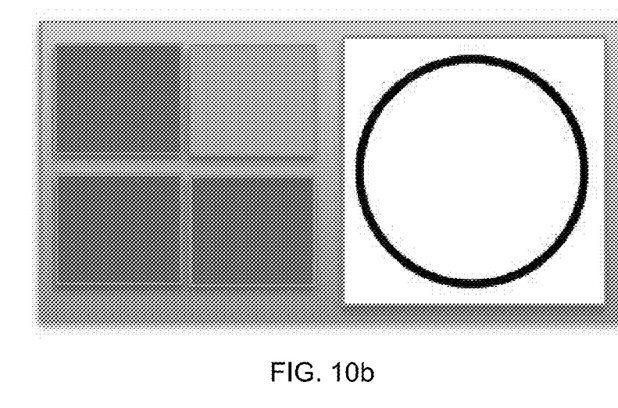

In one embodiment, the plenoptic otoscope is switchable between the depth imaging mode and the spectral imaging mode. In one approach, a clear filter is used for the depth imaging mode and one or more different spectral filters are used for the spectral imaging mode. To switch between the two modes, the filter module 315 could include one section that is clear and another section that contains the spectral filters. The filter module could be translated relative to the primary imaging system, so that the appropriate section is illuminated. An example of this type of filter module is shown in FIG. 10. This filter module could be positioned in a pupil plane conjugate and translated within the pupil plane conjugate to switch between the set of spectral filters and the clear filter. In FIG. 10, the black circle shows the cross-section of the light traveling through the otoscope.

In FIG. 10a, the light travels through the spectral filters, which are depicted as a red rectangle, a blue rectangle, a green rectangle, and a yellow rectangle. The portion of light that passes through a color filter forms an image of the object (within the plenoptic image) that has been filtered by the corresponding color filter. As a result, spectral imaging is enabled. In this example, a plenoptic image is formed, from which four different spectral images of the object (i.e., a red image, a blue image, a green image, and a yellow image) may be extracted.

In FIG. 10b, the filter module is translated relative to the primary imaging system so that the light travels through the clear aperture. This might be used for depth imaging, for example. In this example, a plenoptic image is formed, from which a three-dimensional depth image may be extracted.

This particular filter module has RGB filters for color imaging, plus a yellow filter since yellowish or amber color of tissue is an indicator, and is only shown as an example. In one embodiment, the filter module may include a plurality of different spectral filters. Filters having different colors and/or layouts may also be used in the filter module. For example, see U.S. patent application Ser. No. 13/040,809, filed on May 4, 2011, which is hereby incorporated by reference in its entirety.

Spectral imaging is useful to help distinguish different ear conditions. Some of the ear conditions are shown in FIGS. 1a-c and also in Table 1. For example, AOM is markedly red, OME features amber, and NOE contains gray and pink. In one embodiment, the filter module includes different filters selected to distinguish different ear conditions. Such a filter module is shown in FIGS. 10a-b, e.g., the filter module containing red-green-blue filters and a yellow filter.

Figure 11A:
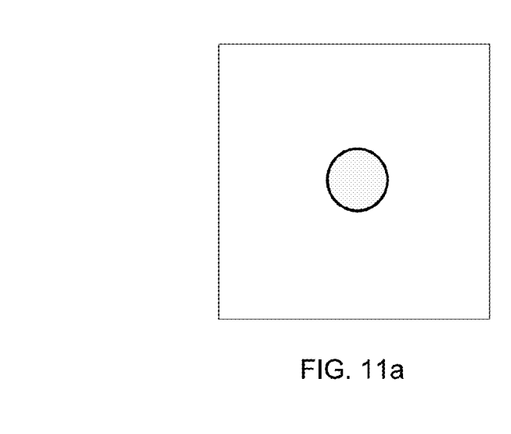
FIGS. 11a-c show additional filter modules.
Figure 11B:
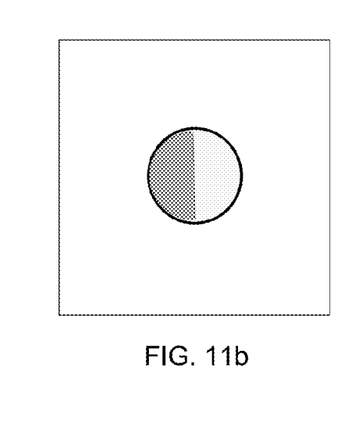

FIGS. 11a-c show some additional filter modules. In FIG. 11a, the filter module has a yellow filter and a transparent area. In FIG. 11b, the filter module has a yellow filter, an amber filter and a transparent area. The sensor array can also be fitted with spectral filters, such as a standard Bayer RGB pattern. Thus, when the filter modules in FIG. 11a or 11b are used with their transparent areas, the Bayer RGB pattern may be used to achieve color imaging. The yellow and amber filters in FIG. 11a and FIG. 11b can be used to extract extra color information. They can be used together with monochromatic sensors and/or RGB sensors (e.g., sensors fitted with a standard Bayer RGB pattern). Such extra color information (e.g., yellow, amber, etc.) can be used to distinguish different ear conditions.

Figure 11C:
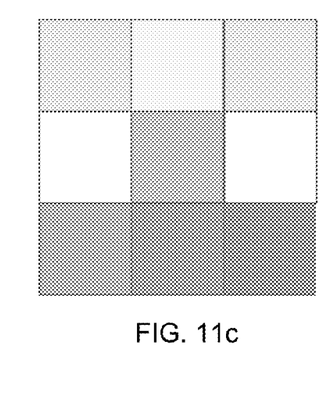

FIG. 11c has an array of filters. The center stripe includes three spectral filters: yellow, amber and a third spectral filter. These can be used for spectral imaging. The top right and top left filters are polarization filters, for example to reduce reflections. The polarization filters may also be useful in extracting illumination characteristics (e.g., when the illumination light has a certain degree of polarization). The middle right and middle left filters are transparent, for example for use in extracting depth information (e.g., depth imaging). The bottom right and bottom left filters are neutral density filters of different densities, for example to increase the dynamic range of the plenoptic otoscope.

Figure 12A:
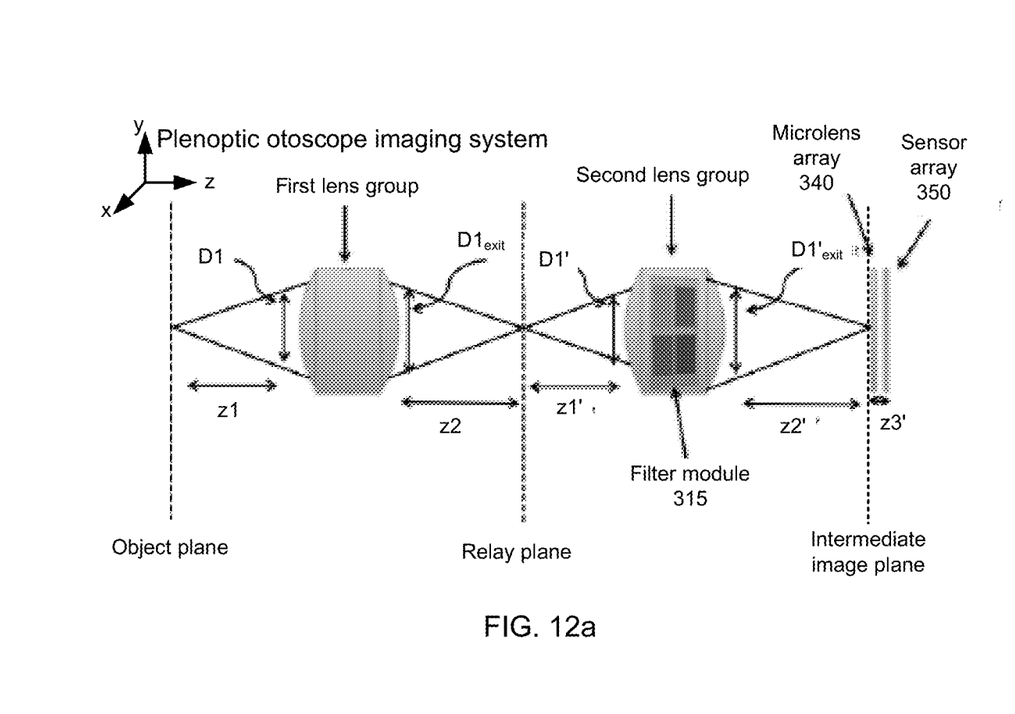
FIGS. 12a-b show a plenoptic otoscope system, introducing notations of dimensions.
Figure 12B:
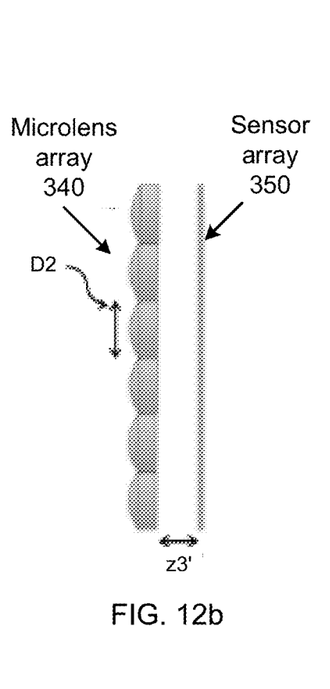

FIGS. 12a-b show a plenoptic otoscope system, introducing notation that will be used to describe different design considerations. FIG. 12a depicts a typical embodiment of a plenoptic otoscope, which includes a primary imaging system and a plenoptic sensor. The primary imaging system includes two lens groups. The first lens group is the otoscope objective, and the second lens group is the relay optics. The plenoptic sensor includes a microimaging array 340 and a sensor array 350. In FIG. 12b, the microimaging array is a microlens array 340, with each microlens having identical optical properties, such as diameter, radius of curvature, material, and thickness. In one embodiment, the diameter of a microlens is chosen to be between 10 and 100 micron.

As shown in FIG. 12a, the object (e.g., a tympanic membrane) is located in an object plane. It is imaged by the first lens group onto a first intermediate image plane (which may be referred to as the relay plane), and then imaged by the second lens group onto a second intermediate image plane where the microlens array 340 is positioned.

In many conventional otoscopes, the magnification of the primary imaging system is set such that the entire tympanic membrane (TM) can be imaged onto the sensor array 350 (as seen in FIGS. 1a-c). Suppose the sensor array 350 has a width W and a height H, and the diameter of the TM is h, then the magnification of the primary imaging system is given by $M=\min(W,H)/h$, where $\min(x,y)$ returns the lesser value of x and y.

The average diameter for the TM of an adult is h=7 mm. Here we define optical system specifications for the example of a ⅓" sensor array with width W=4.6 mm and height H=3.7 mm. For this sensor array, the magnification for the primary imaging system is given by $M=3.7$ mm/7 mm=0.53. Such a magnification is typical for a conventional otoscope. In contrast, a microscope typically has a much larger magnification (>20), and a consumer camera imaging people or natural scenes typically has a much smaller magnification.

The total magnification of the primary imaging system is $M=M1*M2$, where M1 is the magnification of the first lens group, and M2 is the magnification of the second lens group. For illustration purposes, assume M2=1. In other approaches, M2 can be any suitable number other than 1. In the example where M2=1, M1=M. The working F-number, $N_w$, of the first lens group with magnification M is defined as $N_w=(1+M)N$, where N is the F-number of the primary imaging system (i.e., N=f/D1, where D1 is the diameter of the entrance pupil of the primary imaging system, and f is the effective focal length of the primary imaging system.). In one embodiment, the primary imaging system of the plenoptic otoscope is faster than F/8.

The working distance, z1, for the otoscope is the distance between the object and the first lens group. For imaging a TM, a typical working distance is 27-30 mm. The bones behind the TM are located approximately up to a distance of 15 mm from the TM. As a result, the working distance may vary, for example, from 27 mm up to 45 mm. For illustration purposes, assume the working distance z1=30 mm. The entrance pupil is located in the narrow tip of the otoscope close to the first lens group, and is generally smaller than the tip of the otoscope. The tip of an otoscope has a typical diameter of 4-5 mm in order to fit into an ear canal. Let's assume the entrance pupil to have a diameter of 2 mm. Then the effective focal length of the first lens group is f=N*D1=10.4 mm. The second lens group relays the image of the first lens group onto an intermediate image plane, where the microlens array 340 is positioned. The sensor array 350 is positioned at a distance z3' behind the microlens array 340 to capture the plenoptic image.

In one embodiment, the object is located near the hyperfocal distance of the first lens group. The hyperfocal distance is a distance beyond which all objects can be brought into an acceptable focus. Mathematically, the hyperfocal distance may be expressed as $p=f^2/(N c)+f$, where f is the effective focal length, N is the F-number, and c is the circle of confusion diameter limit. In one implementation, the numerical aperture of a microlens matches the image-side numerical aperture of the primary imaging system. That means the working F-number of the primary imaging system matches the F-number of the microlens. Furthermore, the distance z3' is chosen to be equal to the focal length of the microlens. In this configuration, the depth of field is bounded only in one direction, and therefore may be particularly suitable for imaging distant objects.

In one embodiment, the object is placed at a distance z1 away from the entrance pupil of the first lens group. The distance z2 between the exit pupil of the first lens group and the relay plane is determined by the lens equation as: $z2=1/(1/f1-1/z1)$, where f1 is the effective focal length of the first lens group.

The relationship between the first lens group and the second lens group is given by $D1_{exit}/D1'=z2/z1'$, where $D1_{exit}$ is the diameter of the exit pupil of the first lens group, D1' is the diameter of the entrance pupil of the second lens group, and z1' is the distance between the relay plane and the entrance pupil of the second lens group.

The distance z2' between the exit pupil of the second lens group and the intermediate image plane is determined by the lens equation as: $z2'=1/(1/f1'-1/z1')$, where f1' is the effective focal length of the second lens group.

The distance z3' between the microlens array and the sensor array is chosen such that $z3'=z2'\times M_{microlens}$. Here $M_{microlens}=D2/D1'_{exit}$ is the magnification of the microlens sub-system, where D2 is the diameter of the microlens (as shown in FIGS. 12b) and $D1'_{exit}$ is the diameter of the exit pupil of the second lens group. This configuration is specific to imaging with a depth of field bounded in both directions, where the object may not be located near the hyperfocal distance. In comparison, a microscope typically has a much larger magnification (>20), a larger F-number (>15), and a much smaller working distance (a few millimeters).

In one embodiment, the filter module 315 is inserted at the aperture of the second lens group, as depicted in FIG. 12a. The filter module 315 is adjustable in such a way that it can be translated laterally in the x-y plane, which is perpendicular to the optical axis (z axis) of the second lens group. For clarity, the coordinate system is also shown in FIG. 12a. Furthermore, the second lens group may have a diaphragm/iris/shutter attached to the front/back of the filter module 315. This configuration may permit adjustment of the aperture diameter by opening and closing the diaphragm/iris/shutter.

Although the detailed description contains many specifics, these should not be construed as limiting the scope of the invention but merely as illustrating different examples and aspects of the invention. It should be appreciated that the scope of the invention includes other embodiments not discussed in detail above. For example, although the illumination sources have been described in the context of plenoptic otoscopes, they can also be used with conventional otoscopes. The illumination sources can also produce different types of illuminating light, including broadband or narrowband illumination in the ultraviolet, visible and/or near infrared spectrum. Various other modifications, changes and variations which will be apparent to those skilled in the art may be made in the arrangement, operation and details of the method and apparatus of the present invention disclosed herein without departing from the spirit and scope of the invention.

What is claimed is:

1. A plenoptic otoscope comprising:
    a primary imaging system comprising an otoscope objective and relay optics cooperating to form an image of an inside of an ear at an intermediate image plane, the primary imaging system characterized by a pupil plane;
    a plenoptic sensor comprising a microimaging array and a sensor array, the microimaging array positioned at the intermediate image plane and the sensor array positioned at a pupil plane conjugate;
    a filter module positioned at a second pupil plane conjugate, the filter module comprising a central clear area and a plurality of spectral filters arranged around the central clear area, each spectral filter covering a different portion of the second pupil plane conjugate, wherein light that forms the image of the inside of the ear passes simultaneously through the plurality of spectral filters; and
    an illuminator for illuminating the inside of the ear, the illuminator producing illuminating light that propagates through the central clear area of the filter module to the inside of the ear.

2. The plenoptic otoscope of claim 1 further comprising a beamsplitter positioned between the filter module and the plenoptic sensor, the beamsplitter directing the illuminating light from the illuminator towards the inside of the ear.

3. The plenoptic otoscope of claim 2 wherein the beamsplitter is a polarizing beamsplitter.

4. The plenoptic otoscope of claim 1 further comprising a handle, the illuminator located in the handle.

5. The plenoptic otoscope of claim 1 wherein the filter module further comprises four color filters.

6. The plenoptic otoscope of claim 1 wherein the illuminating light comprises white light.

7. The plenoptic otoscope of claim 1 wherein, after propagating through the central clear area, the illuminating light illuminates a speculum tip.

8. The plenoptic otoscope of claim 1 further comprising:
    a computing module that processes a plenoptic image of the inside of the ear, the plenoptic image captured by the sensor array, the computing module producing a three-dimensional depth image of the inside of the ear.

9. The plenoptic otoscope of claim 1 further comprising:
a computing module that processes a plenoptic image of the inside of the ear, the plenoptic image captured by the sensor array, the computing module producing a plurality of spectral images of the inside of the ear.

10. The plenoptic otoscope of claim 1 further comprising:
relay optics, wherein the filter module is located at an aperture between the relay optics and the plenoptic sensor.

11. The plenoptic otoscope of claim 1 wherein the filter module is located at an entrance pupil of the primary imaging system.

12. The plenoptic otoscope of claim 1 further comprising:
relay optics having a plurality of relay lenses, wherein the filter module is located at an aperture between two of the relay lenses.

13. The plenoptic otoscope of claim 1 wherein the plenoptic otoscope is switchable between a depth imaging mode and a spectral imaging mode.

14. The plenoptic otoscope of claim 1 wherein one of the spectral filters is a yellow filter.

15. The plenoptic otoscope of claim 1 wherein one of the spectral filters is an amber filter.

16. The plenoptic otoscope of claim 1 wherein the primary imaging system is faster than F/8.

* * * * *